(12) United States Patent
Duggal et al.

(10) Patent No.: US 11,395,712 B1
(45) Date of Patent: *Jul. 26, 2022

(54) ILLUMINATING SURGICAL DEVICE

(71) Applicant: Illumix Surgical Canada Inc., Bright's Grove (CA)

(72) Inventors: Anil Duggal, Lexington, KY (US); Paul Dobrovolskis, Ancaster (CA); Roel H Kusters, Sittard (NL); Edsger Constant Pieter Smits, Eindhoven (NL); Stephan Harkema, Eindhoven (NL)

(73) Assignee: Illumix Surgical Canada Inc., Bright's Grove (CA)

( * ) Notice: Subject to any disclaimer, the term of this patent is extended or adjusted under 35 U.S.C. 154(b) by 337 days.

This patent is subject to a terminal disclaimer.

(21) Appl. No.: 16/377,219

(22) Filed: Apr. 7, 2019

Related U.S. Application Data

(63) Continuation of application No. 14/819,380, filed on Aug. 5, 2015, now Pat. No. 10,292,784, which is a continuation-in-part of application No. 13/311,031, filed on Dec. 5, 2011, now Pat. No. 9,757,109.

(60) Provisional application No. 61/421,882, filed on Dec. 10, 2010, provisional application No. 61/475,904, filed on Apr. 15, 2011.

(51) Int. Cl.
*A61B 90/30* (2016.01)
*A61B 17/02* (2006.01)
*A61B 17/00* (2006.01)

(52) U.S. Cl.
CPC .............. *A61B 90/30* (2016.02); *A61B 17/02* (2013.01); *A61B 17/0206* (2013.01); *A61B 2017/00946* (2013.01); *A61B 2090/309* (2016.02)

(58) Field of Classification Search
CPC ..... A61B 90/30; A61B 17/02; A61B 17/0206; A61B 2090/309
See application file for complete search history.

(56) References Cited

U.S. PATENT DOCUMENTS

| | | | |
|---|---|---|---|
| 9,400,087 B2 * | 7/2016 | Marquardt | F21V 7/0066 |
| 2006/0069314 A1 * | 3/2006 | Farr | A61B 1/00096 |
| | | | 600/179 |
| 2013/0021798 A1 * | 1/2013 | Chen | F21V 7/00 |
| | | | 362/244 |
| 2014/0221754 A1 * | 8/2014 | Cabaud | A61B 1/0684 |
| | | | 600/178 |

* cited by examiner

*Primary Examiner* — Ellen C Hammond
(74) *Attorney, Agent, or Firm* — Soody Tronson; STLG Law Firm

(57) ABSTRACT

Embodiments of claimed subject matter are directed to an illuminating surgical device comprising an array of illuminating elements and an array of louvers to direct light from the individual illuminating elements toward a surgical field.

18 Claims, 8 Drawing Sheets

(Not to Scale)

500

600

900

ILLUMINATING SURGICAL DEVICE

BACKGROUND

1. Field

This disclosure relates generally to the field of surgical devices and, more particularly, to approaches toward illuminating a surgical area of interest.

2. Information

While performing a surgical procedure, a surgeon may utilize a retractor, which may permit the surgeon to draw lateral and deep layers of tissue away from underlying features. Responsive to the drawing or retracting of lateral and deep layers away from underlying features, a surgeon may focus his or her attention on, for example, repair, manipulation, and/or replacement of body organs, and other anatomical structures including, but not limited to, soft tissue, nerve, venous, arterial, tendinous, and bony structures, and/or may perform numerous other surgical procedures.

However, at times, a surgical instrument may bring about shadowing of light from an overhead source that is intended to illuminate a surgical area of interest. Additionally, other sources of blockage of overhead light may include the surgeon's head, body, and/or hands, for example, and/or one or more body parts of an assistant. Further, other instrumentation in and around the surgical field may obscure the "operator's" view. Accordingly, a surgeon may be required to reposition surgical instruments or overhead lighting or may be required to don or slip on a wearable headlight so as to provide a clear view and unobstructed illumination of an area of interest.

In many instances, light from an overhead source may be tightly directed toward an area of interest. However, since there may be a large distance between surgical instruments and an overhead light source, directed light may introduce optical artifacts, such as shadowing and glare on specific surfaces, which may reduce the visual quality of the illuminating area. Thus, the surgeon may reposition the surgical instrument or shift his or her position in a manner that reduces and/or avoids glare from overhead light sources. Accordingly, virtually any object that is between the light source and the surgical area being viewed may diminish the light in the surgical field hindering the ability of the medical personnel to visualize the important areas.

SUMMARY OF DISCLOSURE

Briefly, particular implementations may be directed to an illuminating surgical device comprising an array of illuminating elements and an array of louvered devices to direct light from individual illuminating elements of the array of illuminating elements toward a target surgical field. In an embodiment, one or more louvered devices of the array of louvered devices may be oriented at an angle approximately in the range of 120 degrees to 150 degrees relative to a substantially planar surface. In an embodiment, one or more louvers of the array of louvered devices may be adjustable between angles such as, for example, 100 degrees to 160 degrees. In an embodiment, a top side of one or more louvers of an array of louvered devices may be coated with a light-absorbing coating to reduce backscatter illumination from adjacent illuminating elements. In another embodiment, at least some of the illuminating elements of the array of illuminating elements are anharmonically spaced relative to one another. Beamwidths of at least some of the illuminating elements of the array of illuminating elements may also be situated so as to overlap with one another.

In an embodiment, one or more louvered devices of the array of louvered devices may be manually oriented at an angle that minimizes backscatter while maximizing illumination area over the target surgical field. In an embodiment, an array of angled reflective surfaces may direct the light from the individual illuminating elements toward the louvers of the array of louvered devices. Angled reflective surfaces may be oriented at an angle approximately in the range of 25 degrees to 55 degrees relative to a substantially planar substrate. In an embodiment, illuminating elements of the array of illuminating elements utilize light emitting diodes and/or organic light emitting diodes having a color temperature approximately in the range of 6500 degrees Kelvin to 7500 degrees Kelvin. However, claimed subject matter may encompass illumination sources having a color temperatures of, for example, as low as 2500 degrees Kelvin, for example, up to, for example, 7500 degrees Kelvin. In particular embodiments, illumination sources may comprise a correlated color temperature approximately in the range of 2500 degrees to 3800 degrees, for example. In an embodiment, light emitting diodes having a color temperature approximately in the range of 2700 degrees to 5000, for example, may be utilized.

In an embodiment, an illuminating surgical device may comprise a substrate layer to accommodate an array of illuminating elements, a reflective layer to accommodate an array of reflective surfaces, a spacing layer to accommodate the array of illuminating elements and the array of reflective surfaces, in which individual illuminating elements of the array of illuminating elements and individual reflective surfaces of the array of reflective surfaces are proximate to one another. An embodiment may further comprise a louvered layer to direct light from individual illuminating elements of the array of illuminating elements toward a target surgical field. In an embodiment, one or more of the reflective layer, the spacing layer, and a louvered layer may be arranged to accommodate anharmonic spacing of illuminating elements of the array of illuminating elements. In an embodiment, the louvered layer may utilize louvers oriented approximately in the range of 120 degrees to 150 degrees relative to a substantially planar surface. Beamwidths of at least some individual illuminating elements may overlap one another. Additionally, at least some reflective surfaces may be oriented at an angle approximately in the range of 30 degrees to 50 degrees relative to a plane of the substrate layer. In an embodiment, at least some reflective surfaces of the array of reflective surfaces may operate to provide approximately lossless reflection of light having a color temperature approximately in the range of 5000 degrees Kelvin to 7500 degrees Kelvin. In embodiments, at least some reflective surfaces of the array of reflective surfaces may operate to provide approximately lossless reflection of light having a color temperature that may include 3500 degrees Kelvin. In an embodiment, a lateral dimension of at least some illuminating elements of the array of illuminating elements may comprise a length approximately in the range of one half a lateral dimension of at least some orifices of the spacing layer. In an embodiment, a louvered layer may be slidable in one or more dimensions so as to bring about redirection of an illumination field emanating from illuminating elements.

In another embodiment, a method of fabricating an illuminating surgical device may comprise affixing anharmonically-spaced illuminating elements atop a substrate layer and affixing a louvered layer atop the substrate layer. The method may further comprise affixing reflective surfaces in close proximity with corresponding anharmonically-spaced illuminating elements. The method may further comprise adjusting one or more of louver angles and orientation angles of the reflective surfaces to control backscatter and illumination of a target surgical field. The method may further comprise encapsulating the louvered layer, after affixing the louvered layer atop the substrate layer, with an encapsulant substantially transparent to light having a color temperature approximately in the wavelength of 5000 degrees Kelvin to 7500 degrees Kelvin.

It should be understood that the aforementioned implementations are merely example implementations, and that claimed subject matter is not necessarily limited to any particular aspect of these example implementations.

BRIEF DESCRIPTION OF DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1:
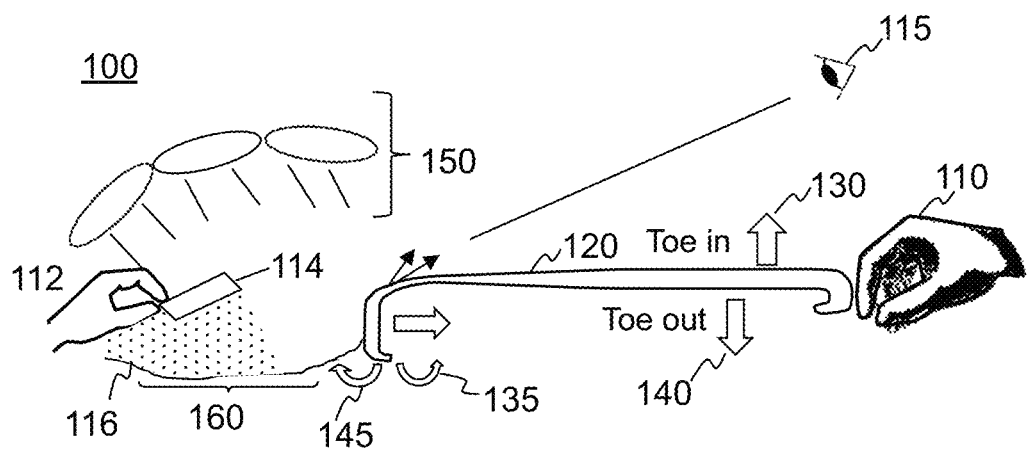
FIG. 1 is an illustration of a surgical retractor in use during a surgical procedure.

Reference is made in the following detailed description to accompanying drawings, which form a part hereof, wherein like numerals may designate like parts throughout to indicate corresponding and/or analogous components. It will be appreciated that components illustrated in the figures have not necessarily been drawn to scale, such as for simplicity and/or clarity of illustration. For example, dimensions of some components may be exaggerated relative to other components. Further, it is to be understood that other embodiments may be utilized. Furthermore, structural and/or other changes may be made without departing from claimed subject matter. It should also be noted that directions and/or references, for example, up, down, top, bottom, and so on, may be used to facilitate discussion of drawings and/or are not intended to restrict application of claimed subject matter. Therefore, the following detailed description is not to be taken to limit claimed subject matter and/or equivalents.

DETAILED DESCRIPTION

Reference throughout this specification to "one example," "one feature," "one embodiment," "an example," "a feature," or "an embodiment" means that a particular feature, structure, or characteristic described in connection with the feature, example or embodiment is included in at least one feature, example or embodiment of claimed subject matter. Thus, appearances of the phrase "in one example," "an example," "in one feature," a feature," "an embodiment," or "in one embodiment" in various places throughout this specification are not necessarily all referring to the same feature, example, or embodiment. Furthermore, particular features, structures, or characteristics may be combined in one or more examples, features, or embodiments.

As previously described, a surgeon may utilize a surgical retractor to draw or pull away lateral and deep layers of tissue to expose one or more underlying features of, for example, a human or animal body. Retraction of lateral and deep layers may permit the surgeon and/or other medical personnel to perform surgical procedures, for example, deep within the human or animal body. However, on occasion, polished, sterilized surgical instruments, such as a retractor, may produce glare from overhead illumination sources. Responsive to observing such glare, a surgeon may be required to shift his or her position and/or reposition one or more surgical instruments. Such adjustment of a surgeon's position and/or repositioning of surgical instruments may reduce a surgeon's efficiency, for example, and may increase the time required to complete a surgical procedure, which may lead to potentially increased postoperative complications associated with prolonged operating times, for example, or may render a procedure more technically difficult. In some instances, such as during very precise surgical procedures involving fine structures of the human body, an amount of overhead light utilized to illuminate a surgical area may be increased so as to permit the surgeon to clearly view the surgical area and to improve surgical safety by, for example, reducing surgeon error, such as inadvertently cutting, suturing, and/or inadvertently damaging vital anatomical structures. However, in these instances, and others, such an increase in ambient and/or overhead illumination may exacerbate glare produced by surgical instruments or create over illumination of the areas surrounding and external to the surgical incision. Presence of additional glare may, in turn, require additional repositioning of one or more surgical instruments, for example or dimming the lights below acceptable levels to reduce glare, for example.

Accordingly, an illuminating surgical retractor may represent an approach toward reducing glare introduced by various overhead and/or ambient surgical lighting systems. In an example embodiment, an illuminating surgical retractor may utilize light emitting diodes (LEDs) and/or organic light emitting diodes (OLEDs), which may serve to diffusely illuminate a surgical field without significant illumination of surrounding areas. In embodiments, use of an illuminating surgical retractor may reduce a need for ambient surgical lighting, such as overhead lighting, which may reduce or eliminate glare introduced by overhead and/or ambient surgical lighting as well as reducing shadowing effects. Such reduction, or elimination of glare entirely, may, for example, reduce annoying eye strain experienced by a surgeon, as well as reduce the need to reposition surgical instruments during surgical procedures, for example. Accordingly, embodiments may bring about a reduction in the time required to perform a surgical procedure as well as an increase in a surgeon's comfort and efficiency.

In embodiments, illuminating elements, which may comprise approximately in the range of 15-30 LEDs, may be affixed in a two-dimensional array across a substrate layer. In particular embodiments, one or more LEDs may be staggered along a third dimension (e.g., depth) to bring about a three-dimensional array of LEDs. In particular embodiments, a two-dimensional or three-dimensional array of surface-mounted, side-firing LEDs, such as those obtained from the Nichia Corporation at 491 Oka, Kaminaka-Cho, Anan-Shi, TOKUSHIMA 774-8601, Japan, may be utilized. Illuminating elements may generate light comprising a color temperature of, for example, approximately in the range of 5000 degrees Kelvin to 7500 degrees Kelvin. In particular embodiments, illuminating elements may generate light comprising a lower color temperature, such as approximately in the range of 3500 degrees Kelvin, which may permit, for example, warming of tissue during a surgical procedure. In other embodiments illuminating elements may generate light outside of the visible wavelengths, such as infrared and/or ultraviolet wavelengths. It should be noted that a variety of LEDs may be utilized and claimed subject matter is not limited to any particular type of LED or LED technology.

As will be described in greater detail herein, illuminating elements, such as LEDs, may be arranged anharmonically in a manner that reduces or eliminates a possibility of noticeable and destructive interference or the over focusing of individual LED elements in the surgical field. Responsive to anharmonic spacing of LED illuminating elements, an illumination area may appear diffuse and uniformly illuminated without significant variation in light hue, color, intensity, for example. Anharmonic spacing of illuminating elements may give rise to additional benefits, and claimed subject matter is not limited in this respect.

In embodiments, a spacing layer may be disposed atop a substrate layer comprising an array of two-dimensional illuminating elements, such as LEDs. However, in some embodiments, LEDs may be staggered in a third dimension, such as depth. A spacing layer may comprise a two-dimensional array of orifices, each of which, for example, may accommodate a corresponding illuminating element of an array of two-dimensional illuminating elements. A spacing layer may additionally accommodate a two-dimensional array of reflective surfaces, which may serve to direct light from illuminating elements in an approximately upward direction away from a substrate layer.

In embodiments, a louvered layer may be disposed atop a spacing layer, which may serve to direct light from a reflective surface, for example, towards a surgical field. A louvered layer may include a two-dimensional array of individual louvers oriented at angles approximately in the range of 120 degrees to 150 degrees relative to a substantially planar horizontal surface. However, it should be noted that embodiments of claimed subject matter may embrace louvers comprising differing orientations with respect to a blade surface, such as angular orientations of less than 120 degrees and angular orientations of greater than 150 degrees, for example. In embodiments, a louvered layer may reduce backscatter, thereby confining an illumination area to encompass a surgical field.

In embodiments, one or more substrate layers, one or more spacing layers, one or more reflective layers, and one or more louvered layers may be constructed so as to form a blade, which may then be encapsulated utilizing a transparent, fluid resistant (e.g., hydrophobic) encapsulant. A transparent encapsulant, as well as reflective layers, louvered layers, and so forth may permit substantially lossless transmission of illumination from illuminating elements. In a particular embodiment, a transparent encapsulant may have intermixed particles which may homogenize light, homogenize a color temperature, and/or provide diffusion of light for example. Such an encapsulant may, for example, include a photo luminescent phosphor, such as cerium-doped yttrium aluminum garnet (CE:YAG) or optically transparent particles comprising a differing refractive index and a matrix of such as $TiO_2$, $SiO_2$, or ZnO, or any combination thereof, for example.

In particular embodiments, many chromophores are possible such as quantum dot particles, which may gain popularity four application in liquid crystal displays. In embodiments, particles small enough to raise an overall refractive index of the matrix (such as less than approximately 30 nm or smaller) may be utilized. Larger particles, such as those greater than approximately 30 nm may not exhibit Rayleigh scattering but may, in some embodiments, exhibit Mie scattering. Such scattering may result in opaque matrices with increased diffuse transmissions, which may bring about a reduction in specular transmittance, for example. In an embodiment, $TiO_2$ particles comprising a radius approximately in the range of 200 nm to 250 nm, for example, comprising an index of refraction approximately in the range of 2.4-2.6, for example, may be utilized as a scatter matrix. In embodiments, zirconia may also be utilized. Although in some embodiments, silica may be added to higher refractive index matrices to reduce a refractive index.

FIG. 1 is an illustration of a surgical retractor, which may embody one or more features of the present invention, in use during a surgical procedure (100). As shown in FIG. 1, surgeon's hand 110 may be utilized to operate surgical retractor 120, such as during a surgical procedure, for example, to draw or retract one or more layers of tissue. Responsive to retraction of lateral and deep layers of tissue, for example, surgical field 160 may be exposed. In addition to drawing or pulling lateral and deep layers of tissue in a manner that exposes surgical field 160, a surgeon may adjust an angular orientation, such as a pitch angle, of surgical retractor 120. In an embodiment, a surgeon may "toe in" a surgical retractor, which may comprise the upward pitching of surgical retractor 120, as shown by arrow 130. Upward pitching of a surgical retractor may give rise to movement of a distal portion of a surgical retractor, such as shown by arrow 135. Likewise, a surgeon may "toe out" a surgical retractor, which may comprise the downward pitching of surgical retractor 120, as shown by arrow 140. Downward pitching of the surgical retractor may give rise to movement of a distal portion of the surgical retractor, such as shown by arrow 145.

Illumination system 150 may comprise one or more overhead illumination devices, such as lamps, spotlights, and so forth. In some instances, such as during the surgical procedure involving a high degree of position, illumination system 150 may generate light having significant intensity, which may, for example, increase a surgeon's eyestrain. Additionally, as intensity of illumination system 150 is increased, stray light from illumination system 150 may produce significant nuisance glare, which may enter surgeon's eye 115. Accordingly, especially during lengthy surgeries, a surgeon may experience eye fatigue, which may reduce his or her efficiency in performing surgical procedures.

Additionally, external lights may generally be poorly focused and thus may be brighter so as to maintain adequate illumination in a narrow surgical field. Responsive to increases in intensity of light, tissues in a surgical field may increase in temperature, which may, for example, bring about desiccation of tissues in the surgical field. Further, increases in intensity of light may give rise to a zone of increased surface temperature in surgical field 160, which may, in some instances, increase fatigue of the surgeon and thus require an operating room to be kept cooler, which may negatively impact condition of the patient.

As shown in FIG. 1, a body part of a surgical assistant, for example, as represented by hand 112, may exemplify an additional source of shadowing, which may impair a surgeon's vision of surgical field 160. For example, hand 112 is shown as manipulating an additional surgical utensil 114, both of which, for example, may bring about an area of shadowing, represented by 116. Accordingly, as previously discussed, several factors may bring about improper illumination of a surgical field. Thus, conventional surgical practice may benefit from one or more embodiments of claimed subject matter.

Figure 2:
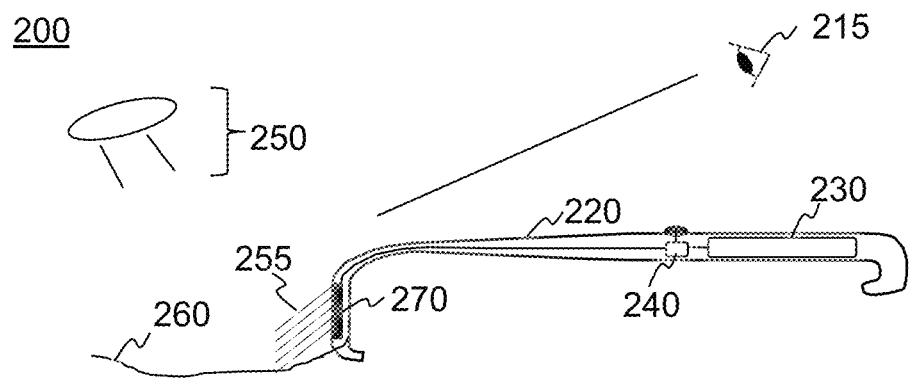
FIG. 2 is an illustration of an illuminating surgical device utilized during a surgical procedure according to an embodiment.

FIG. 2 is an illustration of an illuminating surgical device utilized during a surgical procedure according to an embodiment 200. As shown in FIG. 2, illuminating surgical device 220 may be utilized in place of surgical retractor 120 shown in FIG. 1. In particular embodiments, illuminating surgical device 220 may utilize battery 230 as well as switch 240, which may permit a surgeon to control illumination 255 emanating from blade portion 270. Accordingly, intensity of light emanating from illumination system 250 may be significantly reduced or, in one embodiment, reduced entirely. Hence, shadowing, annoying glare, and/or other stray reflections of light produced by illumination system 250 may be reduced or eliminated entirely.

In particular embodiments, illumination 255 may be oriented at an angle of approximately 135 degrees relative to the vertical plane of blade portion 270. Thus, surgical field 260 may be adequately illuminated, which may permit a surgeon to focus on surgical procedures involving surgical field 260. Accordingly, as a surgeon may toe in or toe out illuminating surgical device 220, or may make other fine adjustments to the position of illuminating surgical device 220, surgical field 260 may remain significantly illuminated without exposing surgeon's eye 215 to extraneous and/or stray illumination from device 220.

Figure 3:
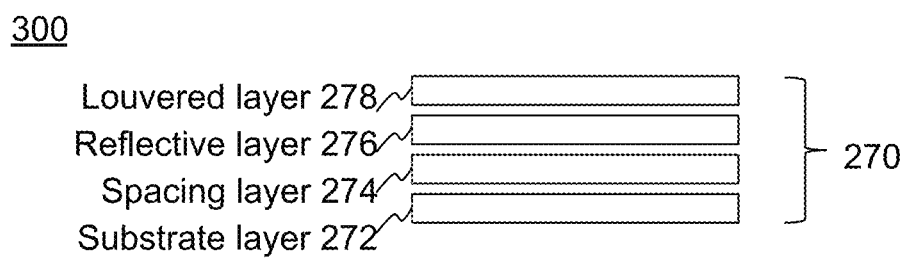
FIG. 3 is a diagram showing a general scheme toward constructing an illuminating surgical device according to an embodiment.

FIG. 3 is a diagram showing a general scheme toward constructing an illuminating surgical device according to an embodiment 300. As shown in FIG. 3, blade portion 270, which may be rotated 90 degrees clockwise from its orientation in FIG. 2, is shown as comprising substrate layer 272, spacing layer 274, reflective layer 276, and louvered layer 278. After assembly of substrate, spacing, reflective, and louvered layers, blade portion 270 may be encapsulated using a transparent hydrophobic encapsulant that may resist materials that may come into contact with an illuminating surgical device such as, for example, fluids from surgical area 260, cleaning solvents and surfactants, and so forth. Transparent encapsulants may be utilized to protect illuminating surgical device 220 from other fluids and/or materials, and claimed subject matter is not limited in this respect.

Figure 4:
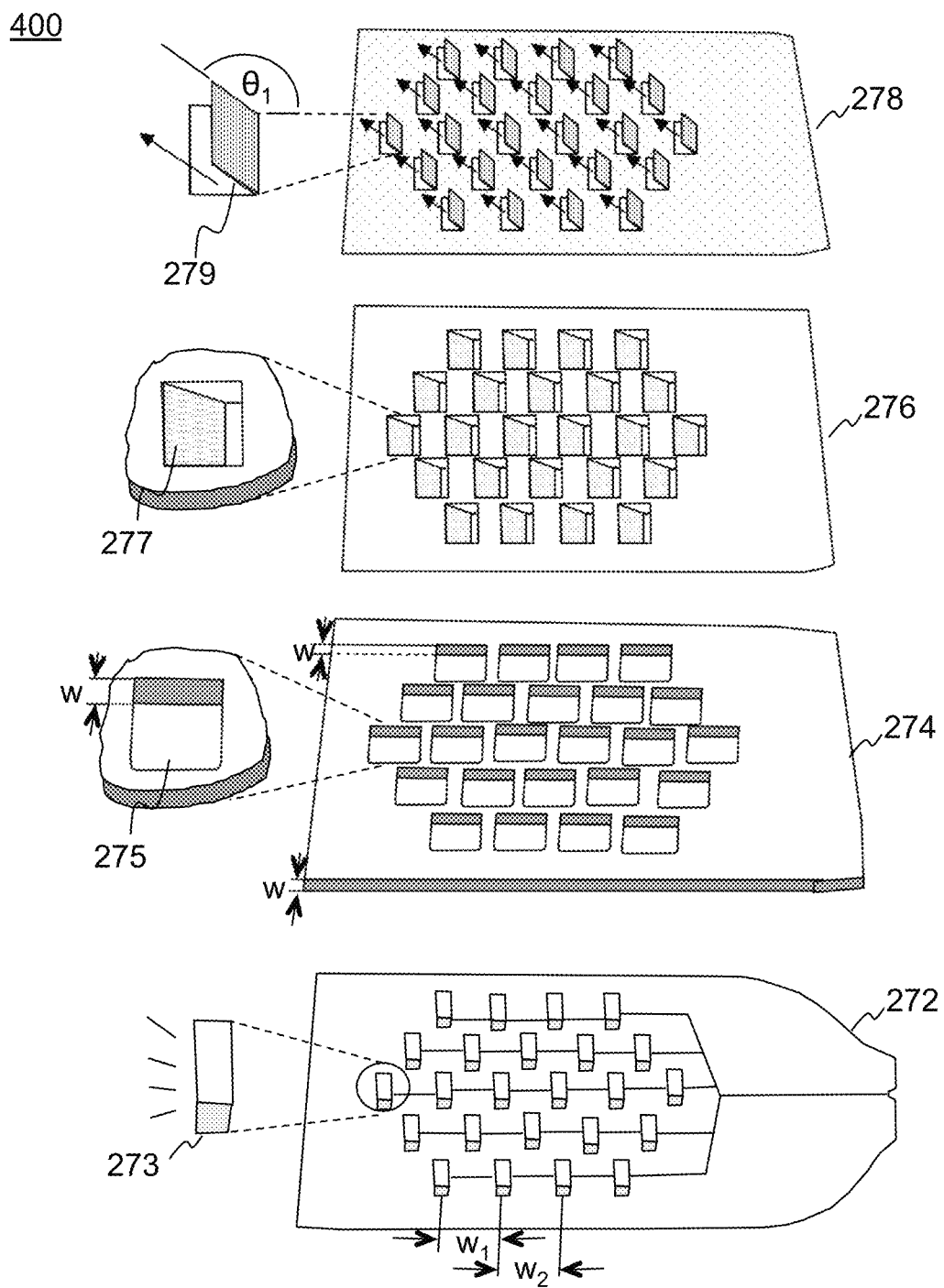
FIG. 4 is an illustration showing details of the construction of an illuminating surgical device according to an embodiment.

FIG. 4 is an illustration showing details of the construction of an illuminating surgical device according to an embodiment 400. Beginning near a bottom portion of FIG. 4, substrate layer 272 may comprise a two-dimensional array of illuminating elements, such as illuminating elements 273. In an embodiment, illuminating elements 273 may comprise side-firing LEDs, which may generate illumination that emanates predominantly from a side, such as the left-hand side, as shown in FIG. 4. However, it should be noted that claimed subject matter is intended to embrace a variety of illumination sources, such as side firing LEDs, end firing LEDs, and other LED types, without limitation.

As shown in FIG. 4, certain adjacent pairs of illuminating elements 273 of a two-dimensional array of illuminating elements may be separated by a distance of, for example, $w_1$, and certain other adjacent pairs of illuminating elements 273 may be separated from one another by a distance of, for example, $w_2$. In embodiments, $w_2$ may be greater than $w_1$, although other embodiments may employ differing spacings, such as, for example, spacings in which $w_1$ may be greater than $w_2$, for example, and claimed subject matter is not limited in this respect. In embodiments, such anharmonic and perhaps three-dimensional spacing (in which certain LEDs disposed atop a substrate layer 272 may be recessed with respect to one another) may be utilized to reduce, or to eliminate entirely, constructive and/or destructive interference brought about by harmonic spacing of illuminating elements 273. In the embodiment of FIG. 4, illuminating elements 273 may be arranged to prevent, for example, occurrence of $n_1\lambda = n_2\lambda$, in an illumination area, which may give rise to "banding," or other noticeable areas of nonuniform intensity which may occur within the illumination area. To reduce the possibility of banding and/or other nonuniform illumination of an area, inter-element spacing ($w_1$) between a first pair of adjacent illuminating elements, which may be represented by $n_1\lambda$ may be made unequal to inter-element spacing ($w_2$) between a second pair of adjacent illuminating elements, which may be represented by $n_2\lambda$. It should be noted, however, that claimed subject matter is not limited to any particular approach toward reducing nonuniform illumination. For example, some embodiments may utilize one or more light diffusers, one or more homogenizers, etc., and claimed subject matter is not limited in this respect. Additionally, in particular embodiments, LEDs of different color temperature and/or wavelength may provide intentional non-uniform illumination, for example.

Spacing layer 274, shown as having width "w" in FIG. 4, may comprise orifices 275, which may be machined into a solid material. In an embodiment, orifices 275 may be arranged in a two-dimensional array so as to be placed atop substrate layer 272. In particular embodiments, illuminating elements 273 may fit within a corresponding orifice. Reflective layer 276, comprising an array of reflectors 277, may be placed atop spacing layer 274 so as to reflect light emanating from illuminating elements 273. In embodiments, reflectors 277 may be sloped downwardly from the plane of the reflective layer so as to fit within orifices 275 of spacing layer 276. In an embodiment, spacing layer 274 and reflective layer 276 may be provided as a single layer comprising injection-molded plastic and may utilize a metal-plated reflective surface.

Louvered layer 278 may be affixed atop reflective layer 276, which may direct light reflected from reflectors 277 toward, for example, surgical area 260 of FIG. 2. As shown in FIG. 2, louvers 279 may be oriented at an approximately 135 degree angle ($\theta_1$) relative to the plane of louvered layer 278. However, as previously noted, claimed subject matter may embrace louvers oriented at a variety of angles, such as angles less than 135 degrees (e.g., 105 degrees, 110 degrees, 115 degrees and, and so forth) and angles greater than 135 degrees (e.g. 140 degrees 145 degrees, and so forth) with respect to the plane of louvered layer 278.

Figure 5:
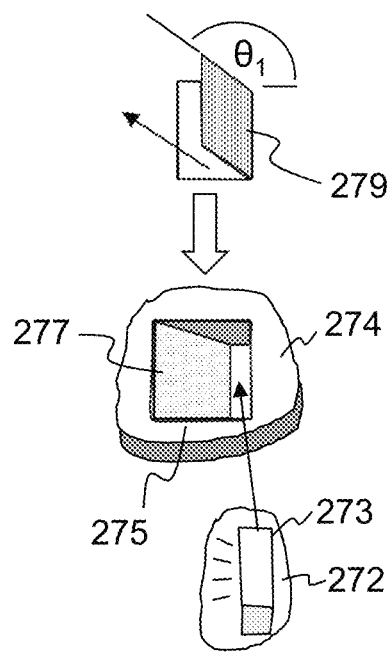
FIG. 5 is an illustration showing integration of individual portions of the illuminating surgical device of FIG. 4 according to an embodiment.

FIG. 5 is an illustration showing integration of individual portions of the illuminating surgical device of FIG. 4 according to an embodiment 500. In FIG. 5, illuminating element 273, which is shown as mounted to a portion of substrate layer 272, is shown as fitting within orifice 275. Thus, light generated by illuminating element 273 may be reflected by reflector 277, also shown as fitting within orifice 275. In FIG. 5, orifice 275 is shown as surrounded by a portion of spacing layer 274. Louver 279, shown as detached from louvered layer 278 for reasons of clarity only, may be placed atop spacing layer 274. Accordingly, the integrated ensemble, comprising layer 278, reflective layer 276, spacing layer 274, and substrate layer 272, may bring about directed lighting of a surgical area without a significant backscattered light. It should be noted, however, that illuminating surgical instrument comprising layers 272, 274, 276, and 278 may be utilized for other purposes, such as a non-surgical purposes, and claimed subject matter is not limited in this respect.

Figure 6:
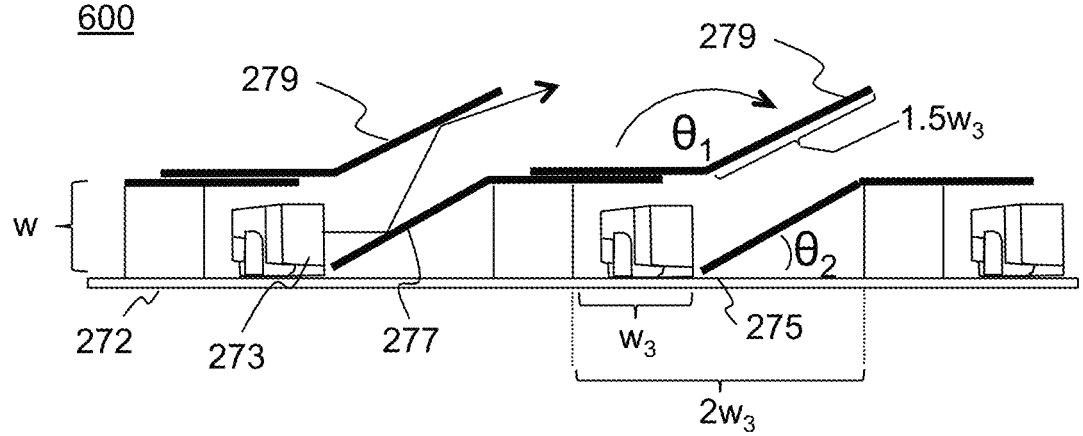
FIG. 6 is a side view showing details of layers of the illuminating surgical device of FIG. 4 according to an embodiment.

FIG. 6 is a side view showing details of layers of the illuminating surgical device of FIG. 4 according to an embodiment 600. In FIG. 6, two of illuminating elements 273 are shown mounted atop substrate layer 272. Although illuminating elements 273 may be illustrated as comprising side-firing LEDs, claimed subject matter is intended to embrace any light-generating device that may be mounted atop a substrate layer and fitted within an orifice. Illuminating element 273 is shown adjacent to a wall having a height w, which may correspond to a thickness dimension of spacing layer 274 of FIGS. 4 and 5. Thus, while disposed within the confines of orifice 275, luminous energy generated by illuminating elements 273 may impinge upon reflectors 277 and the undersides of louvers 279 towards an illumination area.

In embodiments, reflectors 277 may be oriented at an angle $\theta_2$, which may be judiciously selected to increase illumination of a target illumination area, such as a surgical field, for example, without a significant backscatter from the top sides of louvers 279. It is contemplated that $\theta_2$ may comprise a value approximately in the range of 30 degrees and 50 degrees, although in particular embodiments, $\theta_2$ may comprise values less than 30 degrees (e.g. 25 degrees, 20 degrees, and so forth) or may comprise values greater than 50 degrees (e.g., 55 degrees, 60 degrees, and so forth) and claimed subject matter is not limited in this respect. FIG. 6 additionally indicates a horizontal dimension of $w_3$, which corresponds to a horizontal dimension of illuminating elements 273 mounted atop substrate layer 272.

In the embodiment of FIG. 6, the horizontal dimension of orifice 275, which may be formed within spacing layer 274, is shown as comprising twice the horizontal dimension of illuminating element 273. FIG. 6 additionally indicates a linear dimension of louvers 279 as being approximately 1.5 times the horizontal dimension of illuminating elements 273. However, selection of a linear dimension of louvers 279, such as, for example, a linear dimension of 1.5 times the horizontal dimension of illuminating elements 273 may be judiciously selected according to an individual application. Thus, again, the relative dimensions of illuminating element 273, orifice 275, louver 279, and so forth, are provided as an illustrative embodiment, and claimed subject matter is not limited in this respect.

Figure 7:
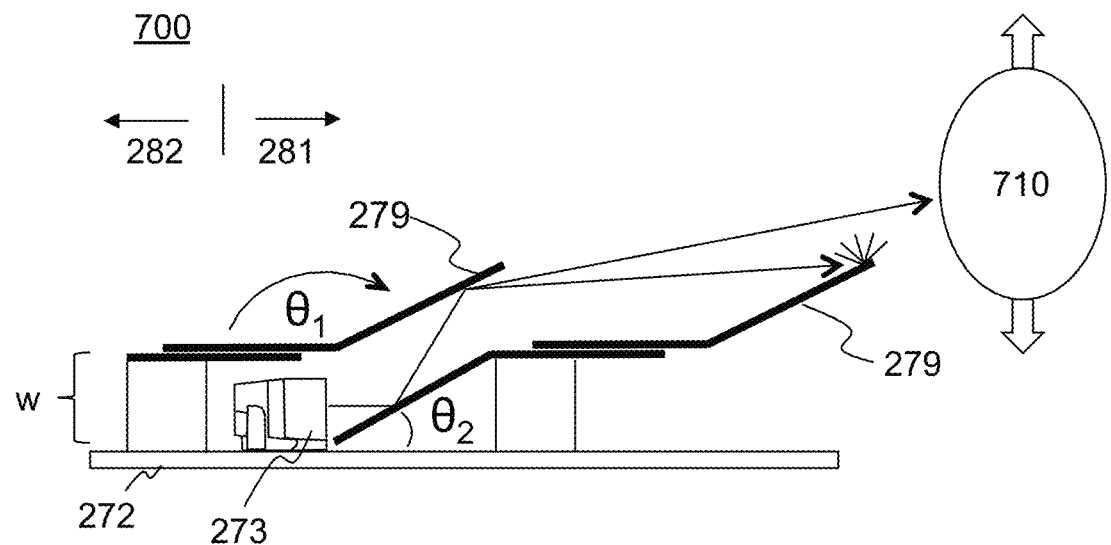
FIG. 7 is a diagram showing movement of an illumination area as a function of orientation of reflective surfaces and louvers according to an embodiment.

FIG. 7 is a diagram showing movement of an illumination area as a function of orientation of reflective surfaces and louvers according to an embodiment 700. As shown in FIG. 7 adjustment of angle $\theta_1$ and $\theta_2$ may serve to redirect light from illuminating element 273 that may backscatter from a top side of louvers 279. In one example, just for the sake of illustration, an increase in angle $\theta_1$, such as from 135 degrees to 145 degrees, may give rise to an increase in light that is backscattered from an adjacent louver 279. However, such an increase in angle $\theta_1$ may also give rise to movement of illumination area 710 in a downward direction. Likewise, adjustment of angle $\theta_1$ may also bring about repositioning of illumination area 710 and influence and amount of the backscattered light from a top surface of an adjacent louver 279. In embodiments, a top side of louvers 279 and/or selected portions of a bottom side of louvers 279, may be coated with a substantially non-reflective material so as to reduce or eliminate backscattered light. As may be inferred from FIG. 7, movement of substrate 272 towards illumination area 710, shown by arrow 281, may decrease the size of area 710. Movement of substrate 272 away from illumination area 710, shown by arrow 282, may increase the size of area 710.

In embodiments, the reflective nature of the internal surfaces of embodiment 700, such as the reflective underside of louvers 279, may give rise to a substantially high contrast ratio between illumination area 710 and the dark, substantially non-reflective topside of louvers 279. A substantially high contrast ratio may prevent excessive glowing of the device during operation and may enhance the directionality of light emanating from illuminating element 273. Accordingly, although area 710 may be illuminated, a negligible amount of light may be reflected back to the surgeon. A reduction in backscattered light, such as may be created by light impinging upon the top side of louvers 279, may be reduced, thereby increasing the visual comfort of the surgeon.

In an embodiment, one or more Fresnel-type lenses may be integrated with, and/or utilized in place of, louvers 279 to efficiently direct light towards illumination area 710, for example. In an implementation, a convex lens may be subdivided so as to form a Fresnel-type lens to obtain a refractive effect similar to a thicker lens, however, by utilizing a much thinner array. Accordingly, a transparent material having a relatively high index of refraction may be utilized. Louvers 279 may be angled at a supercritical angle to permit increased reflection toward illumination area 710. In embodiments, in addition to permitting increased reflection and/or refraction of light toward an illumination area, integration of louvers 279 with Fresnel-type lenses may bring about decreased or negligible backscatter from, for example, top sides of louvers 279.

Figure 8:
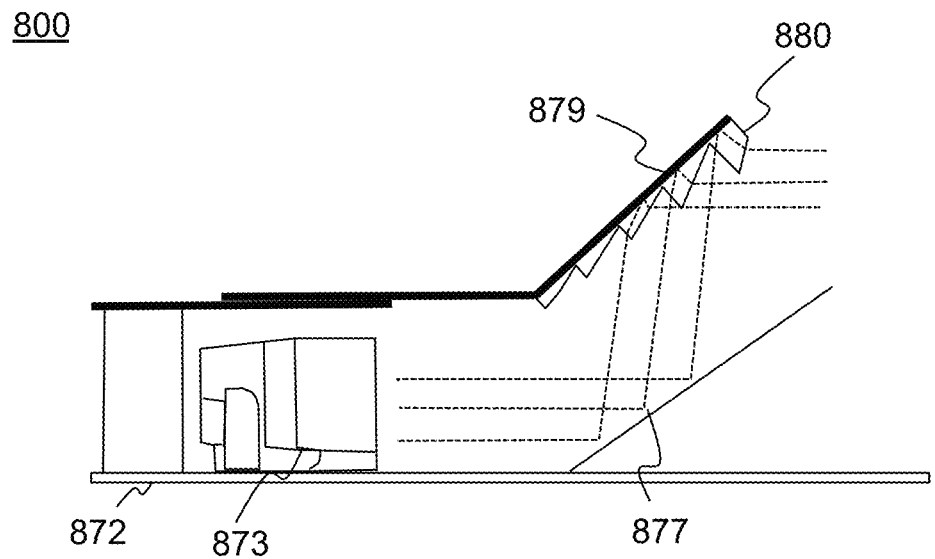
FIG. 8 is a diagram showing a Fresnel-type lens integrated with a reflector according to an embodiment.

FIG. 8 is a diagram showing a Fresnel-type lens integrated with a reflector according to an embodiment 800. In FIG. 8, illuminating element 873, which may be mounted atop substrate layer 872, is shown as illuminating reflector 877. Fresnel-type lens 880, shown affixed to an underside of louvers 979 is shown as operating to bend light from illuminating element 873 towards, for example, an illumination area, such as illumination area 710 of FIG. 7. In embodiments, use of Fresnel-type lenses may permit greater flexibility in selection of, for example, angles $\theta_1$ and $\theta_2$ shown in FIG. 7, which may permit more compact design, of illuminating surgical devices, for example. Further, in particular embodiments may utilize adjustably-angled louvers so as to permit modulation of angle $\theta_1$ of FIG. 7 between angles of, for example, 100 degrees and 160 degrees relative to substrate 872.

In addition to permitting more compact design of the illuminating surgical devices, use of a Fresnel-type lens may permit greater directivity of an illuminating beam emanating from illuminating element 973. Accordingly, such increased directivity may reduce the relative size of illuminating area 710 as well as reducing incidents of stray light impinging on, for example, a top side of adjacent louvers, such as louver 279 of FIG. 7. In addition, a surface portion of top side of louvers 279 may be coated so as to bring about a light-absorbing surface. In embodiments, a top side of louvers 279 may be coated, for example, by depositing light-absorbing materials, which may serve to further diminish backscattered light emanating from illuminating element 273. For example, a top side of louvers 279 may be coated with anodized aluminum, carbon black ink or paint, Catalac black paint, Chemglaze black paint, black lacquers, black velvet paint, polyethylene black plastic, and/or a variety of other materials which may be available from K&K Associates at 10141 Nelson Street, Westminster, Colo. USA. In other embodiments, a deposition process may be utilized to deposit or impart light-absorbing material onto a top side of louvers 279. Light-absorbing properties of a top side of louvers 279 may also be enhanced by increasing surface roughness, such as by scratching and/or abrading, for example. Claimed subject matter is intended to embrace any approach toward reducing and/or eliminating light that is reflected from top sides of louvers 279.

Figure 9:
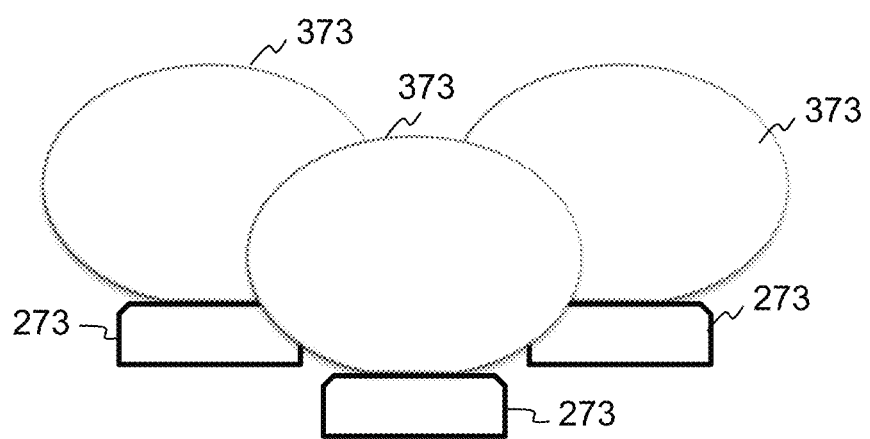
FIG. 9 is a diagram showing overlapping beamwidths of illuminating elements of the illuminating surgical device of FIG. 4 according to an embodiment.

FIG. 9 is a diagram showing overlapping beamwidths of illuminating elements of the illuminating surgical device of FIG. 4 according to an embodiment 800. As mentioned with respect to FIG. 4, certain embodiments may benefit from a reduction in the possibility of banding and/or other nonuniform illumination and area. Thus, in addition to adjustment of inter-element spacing of illuminating elements 273, illuminating elements may also be positioned so as to exhibit overlapping beamwidths, as shown in FIG. 8. In embodiments, such overlapping of beamwidths, such as beamwidth 373, may further reduce the possibility of nonuniform illumination of an illumination area, such as a surgical field.

Figure 10A:
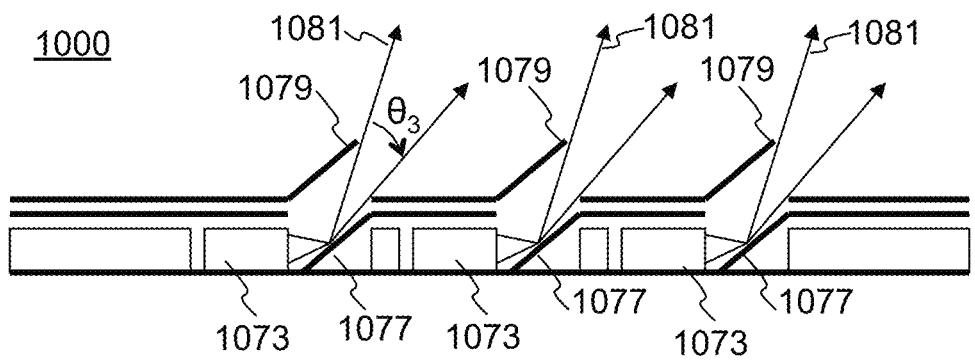
FIGS. 10A, 10B, 10C, 10D, 10E, 10F, and 10G show various embodiments in which a slidable louvered layer may give rise to redirection of an illumination field according to embodiments.
Figure 10B:
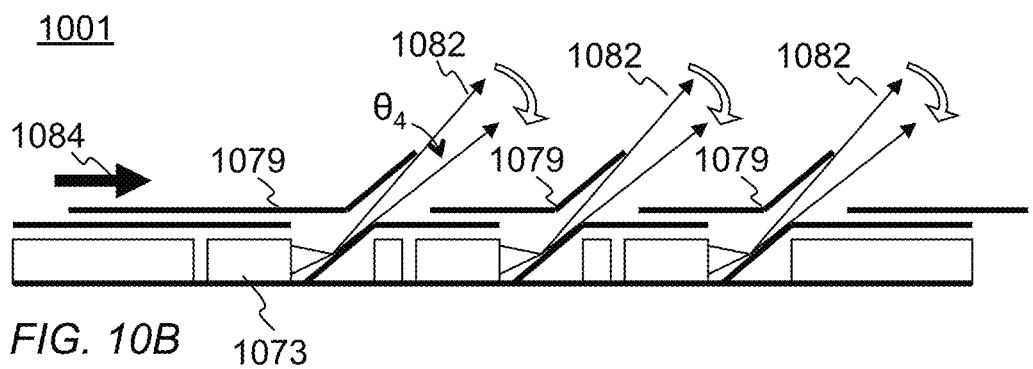
Figure 10C:
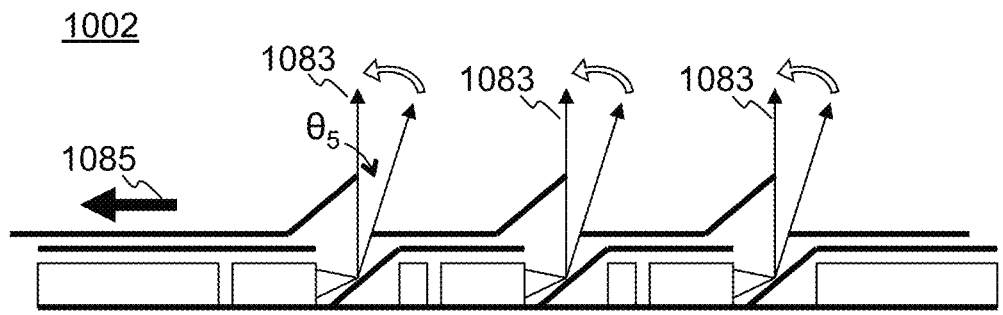

FIGS. 10A, 10B, and 10C are diagrams showing movement of a louver layer, which may operate to redirect light from illumination sources according to an embodiment. For example, in embodiment 1000 of FIG. 10A, light from illumination sources 1073 may be reflected upwards by, for example, reflective layer 1077. Light from reflective layer 1077 may be re-directed into a cone-shaped area given, for example, by angle $\theta_3$, for example. In embodiments, illumination within the cone-shaped area corresponding to angle $\theta_3$ may correspond to an illumination area above and slightly to the right of an imaginary vertical line extending normal to the plane embodiment 1000.

In embodiment 1001 (FIG. 10B) louver layer 1079 is shown as shifted slightly to the right of its position shown in embodiment 1000 (FIG. 10A). In embodiments, such shifting of louver layer 1079 in the direction of arrow 1084 may bring about confinement of light rays emanating from illuminating elements 1073 to an area corresponding to $\theta_4$. In embodiments, illumination within the cone-shaped area corresponding to angle $\theta_4$ may correspond to an illumination area above and considerably to the right of an imaginary vertical line extending normal to the plane of embodiment 1001.

In embodiment 1002 (FIG. 10C) louver layer 1079 is shown shifted slightly to the left of its position shown in embodiment 1000 (FIG. 10A). In embodiments, such shifting of louver layer 1079 in the direction of arrow 1085 may bring about confinement of light rays emanating from illuminating elements 1073 to an area corresponding to $\theta_5$. In embodiments, illumination within the cone-shaped area corresponding to angle $\theta_5$ may correspond to an illumination area directly above and very slightly to the right, for example, of an imaginary vertical line extending normal to the plane of embodiment 1002.

Figure 10D:
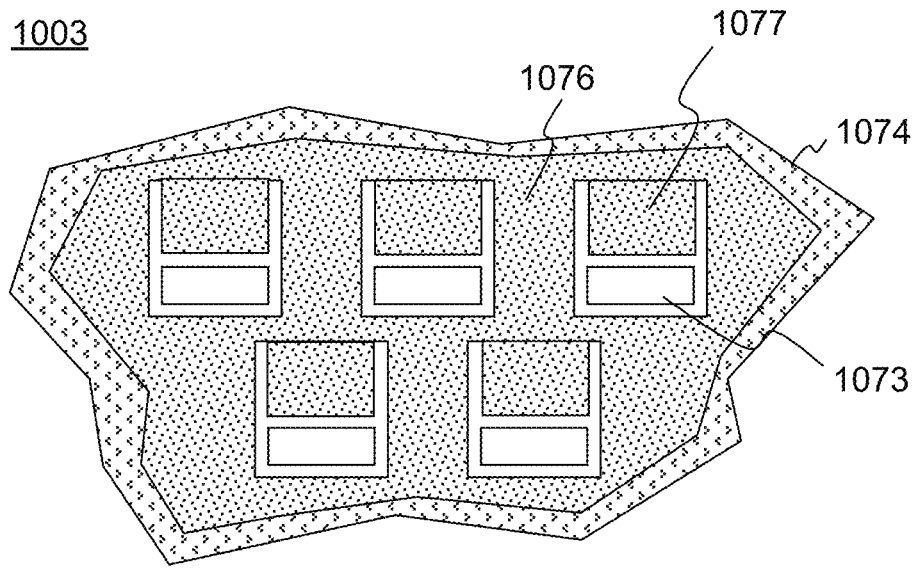

FIG. 10D is an illustration showing the various layers and/or structures that may be utilized in an illuminating surgical device according to an embodiment. Embodiment 1003 of FIG. 10D may correspond, for example, to one or more of embodiments 1000, 1001, or 1002. In embodiment 1003 of FIG. 10D, spacing layer 1074 may correspond to spacing layer 274, for example, shown in FIG. 4. Reflective layer 1076 may be disposed atop spacing layer 1074, which may comprise reflectors 1077, such as shown in FIG. 10D. In one embodiment, reflectors 1077 may be sloped towards illuminating elements 1073 in a manner similar, for example, to the sloping of reflectors 277 in the direction of illuminating elements 273 as shown in FIG. 5.

Figure 10E:
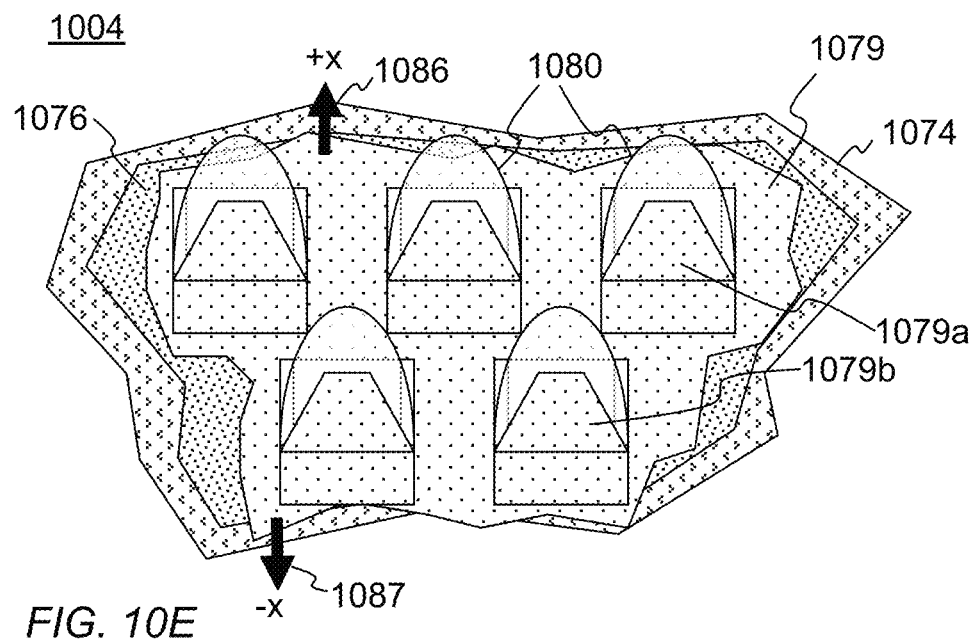

FIG. 10E shows louver layer 1079 disposed atop reflective layer 1076 in accordance with an embodiment 1004. FIG. 10E also shows example louvers 1079a and 1079b, which may be permitted to slide over reflectors 1077. In an embodiment, movement of louver layer 1079 in the direction of arrow 1086 may bring about redirection of example illumination fields 1080 in a +x direction. Also in an embodiment, movement of louver layer 1079 in the direction of arrow 1087 may bring about redirection of example illumination fields 1080 in a -x direction.

Figure 10F:
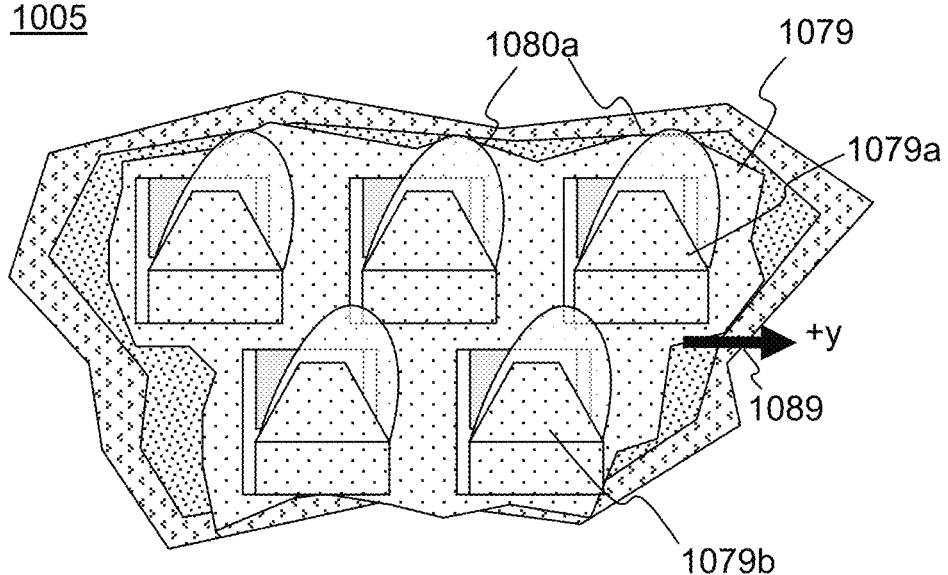
Figure 10G:
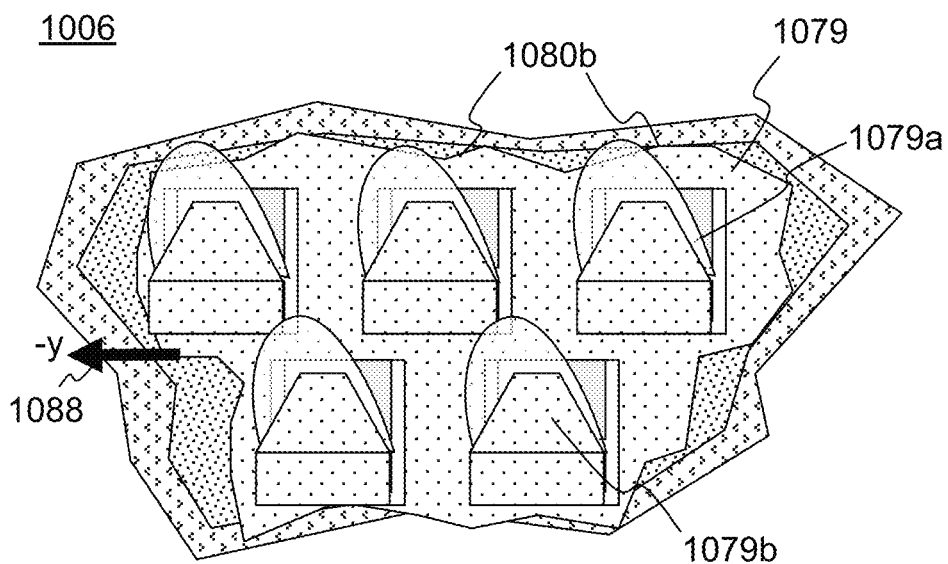

FIG. 10F shows louver layer 1079, including louvers 1079a and 1079b, for example, moved in a +y direction, which brings about redirection of illumination field 1080a to the right. FIG. 10G shows louver layer 1079, including louvers 1079a and 1079b moved in a -y direction, which brings about redirection of illumination field 1080b to the left. Accordingly, louvers may be slid in +y, thereby permitting fine adjustment of illumination fields, such as illumination fields 1080a and 1080b.

Although particular illuminating elements, such as illuminating elements 273, have been described, it should be noted that theoretical efficiency of both light emitting diodes and/or organic light emitting diodes may be similar and may be based on a desired spectral response. In embodiments, efficiencies of illuminating elements may be reduced if a specific correlated color temperature range and/or color quality is utilized. Correlated color temperature ranges (e.g., "cool" or "warm" color temperatures) may be tuned, for example, by modulating chemical compounds utilized in light-emitting devices. In metal-constructed illuminating surgical devices, metal may be used as a heat sink, which may permit use of illumination sources that generate increased waste heat. Accordingly, heating of the illuminating surgical device may not be of significant importance. If directional light from an illuminating surgical device is utilized, in some embodiments, organic light emitting diodes may not represent a prudent design choice. This may be of particular importance in applications in which diffuse light may be preferred over applications in which light is directed toward particular illumination areas.

The terms, "and", "or", and "and/or" as used herein may include a variety of meanings that also are expected to depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, and/or characteristic in the singular and/or may be used to describe a plurality or some other combination of features, structures and/or characteristics. Though, it should be noted that this is merely an illustrative example and claimed subject matter is not limited to this example.

While there has been illustrated and/or described what are presently considered to be example features, it will be understood by those skilled in the relevant art that various other modifications may be made and/or equivalents may be substituted, without departing from claimed subject matter. Additionally, many modifications may be made to adapt a particular situation to the teachings of claimed subject matter without departing from the central concept(s) described herein. Therefore, it is intended that claimed subject matter not be limited to the particular examples disclosed, but that such claimed subject matter may also include all aspects falling within appended claims and/or equivalents thereof.

What is claimed is:

1. An illuminating surgical device, comprising:
an array of illuminating elements;
an array of slanted reflectors, individual reflectors of the array of slanted reflectors in correspondence with, and slanted in the direction of, individual illuminating elements of the array of illuminating elements, the slanted individual reflectors being mounted coplanar with the individual illuminating elements; and
an array of louvers, individual louvers of the array of louvers having a reflective underside to direct light originating from the individual illuminating elements of the array of illuminating elements toward a target surgical field,
the individual louvers of the array of louvers being oriented at an angle that reduces backscatter and increases illumination at the target surgical field.

2. The illuminating surgical device of claim 1, wherein the individual louvers of the array of louvers, are adjustable between angles of about 100 degrees to about 160 degrees relative to a substantially planar surface of the array of illuminating elements.

3. The illuminating surgical device of claim 2, wherein a top side of the individual louvers of the array of louvers are coated with a non-reflective coating.

4. The illuminating surgical device of claim 1, wherein at least some illuminating elements of the array of illuminating elements are anharmonically spaced relative to one another.

5. The illuminating surgical device of claim 1, wherein beamwidths of at least some illuminating elements of the array of illuminating elements are situated so as to overlap with one another.

6. The illuminating surgical device of claim 1, wherein, the array of slanted individual reflectors is oriented at an angle to direct the light from corresponding illuminating elements of the array of illuminating elements towards corresponding louvers of the array of louvers.

7. The illuminating surgical device of claim 6, wherein at least some of the slanted individual reflectors are oriented at an angle approximately in the range of 25 degrees to 55 degrees relative to a substantially planar surface of the array of illuminating elements.

8. The illuminating surgical device of claim 1, wherein illuminating elements of the array of illuminating elements utilize light emitting diodes having a color temperature approximately in the range of 6500 degrees Kelvin to 7500 degrees Kelvin.

9. The illuminating surgical device of claim 1, wherein one or more reflectors of the array of reflective devices comprises a Fresnel-type lens on an underside of the one or more reflectors.

10. An illuminating surgical device, comprising:
a substrate layer to accommodate an array of illuminating elements;
a spacing layer to accommodate the array of illuminating elements and an array of slanted reflectors, individual slanted reflectors of the array of slanted reflectors being mounted coplanar, and in correspondence with, individual illuminating elements of the array of illuminating elements; and
a louver layer comprising an array of louvers, each louver having a reflective underside, to direct light from individual slanted reflectors of the array of slanted reflectors toward a target surgical field, the louver layer to direct the light from the individual reflectors in a manner that reduces backscatter and increases illumination at the target surgical field.

11. The illuminating surgical device of claim 10, wherein one or more louvers of the array of louvers is adjustable between angles of about 100 degrees to 160 degrees relative to a substantially planar surface of the array of illuminating elements.

12. The illuminating surgical device of claim 11, wherein one or more louvers of the array of louvers comprises a Fresnel-type lens on an underside of the one or more louvers reflectors.

13. The illuminating surgical device of claim 10, wherein a top side of one or more louvers of the array of louvers is coated with a light-absorbing coating to reduce the backscatter.

14. The illuminating surgical device of claim 10, wherein at least some illuminating elements of the array of illuminating elements are anharmonically spaced relative to one another.

15. The illuminating surgical device of claim 10, wherein beamwidths of at least some illuminating elements of the array of illuminating elements are situated so as to overlap with one another.

16. The illuminating surgical device of claim 10, wherein the array of slanted individual reflectors operate to direct the light from the individual illuminating elements towards a corresponding louver of the array of louvers.

17. The illuminating surgical device of claim 16, wherein at least some of the individual slanted reflectors of the array of slanted reflectors are oriented at an angle approximately in the range of 25 degrees to 55 degrees relative to a substantially planar surface of the array of illuminating elements.

18. The illuminating surgical device of claim 10, wherein illuminating elements of the array of illuminating elements utilize light emitting diodes having a color temperature approximately in the range of 6500 degrees Kelvin to 7500 degrees Kelvin.

* * * * *